United States Patent [19]

DiPietro

[11] Patent Number: 4,617,185

[45] Date of Patent: Oct. 14, 1986

[54] IMPROVED DEODORANT STICK

[75] Inventor: Dawn M. DiPietro, Fairfield, Ohio

[73] Assignee: The Procter & Gamble Company, Cincinnati, Ohio

[21] Appl. No.: 630,790

[22] Filed: Jul. 13, 1984

[51] Int. Cl.$^4$ .............................................. A61K 17/32
[52] U.S. Cl. ................................ 424/65; 424/DIG. 5
[58] Field of Search ....................... 424/DIG. 5, 65, 63

[56] References Cited

U.S. PATENT DOCUMENTS

| 2,732,327 | 1/1956  | Teller et al. | 167/90  |
|-----------|---------|---------------|---------|
| 2,857,315 | 10/1958 | Teller        | 167/90  |
| 2,900,306 | 8/1959  | Slater        | 167/90  |
| 2,970,083 | 1/1961  | Bell          | 424/68  |
| 3,740,421 | 6/1973  | Schmolka      | 424/65  |
| 3,867,533 | 2/1975  | Schmolka      | 424/258 |
| 4,089,814 | 5/1978  | Schmolka      | 252/522 |
| 4,154,816 | 5/1979  | Roehl et al.  | 424/68  |
| 4,226,889 | 10/1980 | Yuhas         | 424/59  |
| 4,252,789 | 2/1981  | Broad         | 424/65  |
| 4,268,498 | 5/1981  | Gedeon et al. | 424/59  |

FOREIGN PATENT DOCUMENTS

| 0024365 | 3/1981  | European Pat. Off. | 424/DIG. 5 |
| 0058474 | 8/1982  | European Pat. Off. | 424/DIG. 5 |
| 1042499 | 9/1966  | United Kingdom     | 424/357    |
| 1173743 | 12/1969 | United Kingdom     | 424/63     |
| 1207438 | 9/1970  | United Kingdom     | 424/68     |
| 2020974 | 11/1979 | United Kingdom     | 424/DIG. 5 |

OTHER PUBLICATIONS

Ash, A Formulary of Cosmetic Preparations, 1977, pp. 16 to 18, 356 and 357.

*Primary Examiner*—Dale R. Ore
*Attorney, Agent, or Firm*—Richard C. Witte; John V. Gorman; Douglas C. Mohl

[57] ABSTRACT

Stable soap gel cosmetic stick compositions comprising a polyhydric aliphatic alcohol, soap and di-isopropyl adipate. Such cosmetic sticks are easily processed as well as possessing good application properties.

11 Claims, No Drawings

IMPROVED DEODORANT STICK

TECHNICAL FIELD

The present invention relates to cosmetic compositions in the form of solid sticks. The compositions herein comprise a polyhydric alcohol, soap and di-isopropyl adipate.

BACKGROUND ART

Attempts have been made to realize cosmetic sticks which deliver active ingredients to the skin such as deodorant materials via a vehicle which glides easily over the skin surface and which imparts a cooling sensation to the skin both during and after application. One approach has been to form gels based on soap and alcohol. Such gels are disclosed for example in U.S. Pat. No. 2,732,327, Jan. 24, 1956 to Teller; U.S. Pat. No. 2,857,315, Oct. 21, 1958 to Teller; U.S. Pat. No. 2,900,306, Aug. 18, 1959 to Slater; and U.S. Pat. No. 2,970,083, Jan. 31, 1961 to Bell.

While soap gels are old as evidenced by the above patents, such gels are not completely satisfactory. Generally, soap gels require considerable time to set up and often exhibit syneresis at elevated temperatures. This necessitated work to be done to find solutions to these problems.

One solution developed involved the inclusion of an ethylene oxide and/or propylene oxide condensation product. Such products are disclosed in European Patent Application No. 0024365, published Mar. 4, 1981.

While the inclusion of the condensation product provided for reduced set-up times there still existed the need for improving application cosmetics (e.g., less hairpull, drag and stickiness). The present invention has found that the use of a particular emollient provides such benefits.

It is, therefore, an object of the present invention to provide cosmetic soap gel sticks which have good application cosmetics, and in a preferred form, favorably low set-up times and limited syneresis.

It is a further object of the present invention to provide such cosmetic sticks which effectively deliver deodorant materials to the skin.

It has been surprisingly discovered that the above objectives can be realized by formulating a stick comprising the ingredients described below.

All percentages used herein are by weight of the total composition unless otherwise designated.

DISCLOSURE OF INVENTION

The present invention relates to cosmetic stick compositions comprising from about 6% to about 70% of a polyhydric aliphatic alcohol, from about 3% to about 10% of a soap and from about 10% to about 60% of di-isopropyl adipate.

DETAILED DESCRIPTION OF THE INVENTION

The essential elements of the cosmetic gel sticks of the present invention as well as optional components, composition preparation, and composition use are discussed in detail below:

Polyhydric Aliphatic Alcohol

An essential component of the present cosmetic gel stick compositions is a polyhydric aliphatic alcohol containing 2 or 3 carbon atoms and from 2 to 3 hydroxyl groups. The polyhydric aliphatic alcohol component of the stick comprises from about 6% to about 70%, preferably from about 15% to 30%, by weight of the composition.

Suitable polyhydric alcohols for use in the gel compositions herein include ethylene glycol, propylene glycol, trimethylene glycol, and glycerine. The most preferred polyol is propylene glycol and mixtures may be used.

Soap

Another essential component of the compositions herein is a gel forming agent. The gel forming agents used herein are preferably the sodium, potassium and aluminum salts (i.e., soaps) of fatty acids containing from about 12 to 22 carbon atoms and mixtures of such fatty acids.

Soaps generally comprise from about 3% to about 10% by weight, preferably from about 3% to about 8% by weight of the composition. If soap concentrations much lower than those specified are employed, the gels formed tend to be dimensionally unstable and tend to deform at summertime temperatures. If concentrations of soap much above those specified are utilized, the gels formed tend to be too hard and do not exhibit desirable glide and application characteristics.

The fatty acid portion of the soap gel forming agents should preferably be essentially pure saturated or unsaturated higher fatty acids having a $C_{14}$ to $C_{18}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the gel forming agents herein include myristic, palmitic, stearic, oleic, linoleic, linolenic, margaric and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids, and greases. Conventional fractionation and/or hydrolysis techniques can be employed if necessary to obtain the requisite types of fatty acids from such materials.

Preferred fatty acid soap type gel forming agents include sodium stearate, sodium palmitate, potassium stearate, potassium palmitate, sodium myristate and aluminum monostearate. Mixtures of soaps may also be used. The most preferred gel forming agent is sodium stearate.

Di-Isopropyl Adipate

The third essential component for use in the present compositions is di-isopropyl adipate. This item of commerce is present at a level of from about 10% to about 60%, preferably from about 15% to about 40%. The inclusion of di-isopropyl adipate in the present compositions provides for less stickiness.

Optional Components

The instant stick compositions can contain a variety of optional ingredients suitable for improving composition efficacy, stability, cosmetics and/or aesthetics. Such optional components include deodorant materials, perfumes, dyes, pigments, coloring agents and the like.

A highly preferred optional component for use in the instant compositions is an ethylene oxide and/or propylene oxide condensation product having the following formula:

$$R(OC_2H_4)_a(OC_3H_6)_bOH$$

wherein R is either hydrogen or a hydrocarbon chain having from about 2 to 20 carbon atoms, preferably from about 4 to 18, a and b are each from 0 to 35 and a+b is from 5 to 35.

Examples of such products are a condensate of about 14 moles of propylene oxide with about one mole of butyl alcohol sold by Union Carbide under the name Fluid AP$^R$; a polypropylene glycol having a molecular weight of 1200; a polyethylene glycol having a molecular weight of 420; a condensate of 20 moles of ethylene oxide and 5 moles of propylene oxide with one mole of cetyl alcohol; and a condensate of 15 moles of propylene oxide with one mole of stearyl alcohol. The preferred condensate is Fluid AP$^R$.

The amount of the condensation product in the compositions of the present invention, if present, is from about 10% to about 60%, preferably from about 15% to about 40% by weight of the composition.

Another preferred optional component for use in the instant compositions is a fatty alcohol and/or an ethoxylated fatty alcohol. Such alcohols generally have from about 10 to about 15 carbon atoms and include, but are not limited to, myristyl alcohol, dodecyl alcohol, coconut fatty alcohol, ethoxylated forms of these alcohols wherein from about 2 to about 6 ethoxy groups are present and mixtures thereof. The amount of the alcohol in the instant compositions, if present, is from about 4% to about 30%, preferably from about 5% to about 20%.

Another optional ingredient of the instant compositions is a conventional deodorant material. Suitable deodorants include bacteriostatic quaternary ammonium compounds such as cetyltrimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N-hyristoyl glycine, potassium N-lauroyl sarcosine and stearyl tri-methyl ammonium chloride. If present, deodorants generally comprise from about 0.1% to 1.0% by weight of the composition.

Another optional component is a short chain monohydric alcohol in an amount from about 0.1% to about 50.0%, preferably from about 1.0% to about 40.0%. Suitable alcohols include methanol, ethanol, N-propanol and ispropanol. The preferred alcohol is ethanol.

Other optional ingredients such as perfumes, dyes, pigments, coloring agents and the like, if present, comprise from about 0.1% to 1.5% by weight of the compositions.

METHOD OF MANUFACTURE

The gel sticks of the present invention are made by combining the ingredients in liquid form and pouring the mixture into a form having the desired shape. The present gel may be used as the gel portion of the antiperspirant sticks described and claimed in U.S. Pat. No. 4,202,879, May 13, 1980 to Shelton, incorporated herein by reference. A preferred antiperspirant stick is where the present gel forms a shell around the antiperspirant core.

COMPOSITION USE

The gel sticks herein are used by the consumer by rubbing the stick on the area of the body where application is desired. In the case of a deodorant stick the stick is rubbed in the axilla area to apply the deodorant agent.

EXAMPLES I–IV

Given below are examples of compositions within the scope of the present invention which were prepared.

| Formula Component | Wt. % | | | |
|---|---|---|---|---|
| | I | II | III | IV |
| Propylene glycol | 20.00 | 20.00 | 26.18 | 20.00 |
| Fluid AP ®$^1$ | 25.85 | 44.65 | — | — |
| Ethanol | 8.50 | 8.50 | 7.50 | 8.50 |
| Sodium stearate | 6.25 | 6.25 | 6.24 | 6.25 |
| Di-isopropyl adipate | 28.80 | 10.00 | 57.68 | 28.80 |
| Myristyl alcohol | 8.00 | 8.00 | — | 8.00 |
| Witconol APM ®$^2$ | — | — | — | 25.85 |
| Deodorant material | 0.30 | 0.30 | 0.30 | 0.30 |
| Dye | 1.30 | 1.30 | 1.30 | 1.30 |
| Fragrance | 1.00 | 1.00 | 0.80 | 1.00 |
| | 100.00 | 100.00 | 100.00 | 100.00 |

$^1$Condensation product of one mole of butyl alcohol with 14 moles of propylene oxide supplied by Union Carbide Corporation.
$^2$Condensation product of one mole of myristyl alcohol with three moles of propylene oxide supplied by Witco Chemical Company.

EXAMPLE V

The following composition of the present invention is prepared.

| Component | Wt. % |
|---|---|
| Propylene glycol | 23.97 |
| Fluid AP | 28.84 |
| Ethanol | 7.50 |
| Sodium stearate | 8.25 |
| Di-isopropyl adipate | 10.00 |
| Dodecyl alcohol | 18.84 |
| Deodorant material | 0.30 |
| Dye | 1.30 |
| Fragrance | 1.00 |
| | 100.00 |

EXAMPLE VI

The following composition of the present invention is also prepared.

| Component | Wt. % |
|---|---|
| Propylene glycol | 20.63 |
| Fluid AP | 27.12 |
| Ethanol | 7.52 |
| Sodium stearate | 5.88 |
| Di-isopropyl adipate | 28.85 |
| Neodol 23-3$^1$ | 10.00 |
| | 100.00 |

$^1$C$_{12}$–C$_{13}$ linear alcohol ethoxylate - Shell Chemical Company

EXAMPLE VII

The following composition of the present invention is prepared.

| Component | Wt. % |
|---|---|
| Propylene glycol | 28.57 |
| Fluid AP | 28.84 |

-continued

| Component | Wt. % |
| --- | --- |
| Ethanol | 7.75 |
| Sodium stearate | 6.00 |
| Coconut fatty alcohol | 18.84 |
| Di-isopropyl adipate | 10.00 |
| | 100.00 |

EXAMPLE VIII

To measure the performance of compositions representative of the present invention, three paired evaluations were conducted. The three compositions of this invention were those identified as I, II and III above. The comparison composition in each instance was as follows:

| Component | Wt. % |
| --- | --- |
| Propylene glycol | 26.18 |
| Ethanol | 7.50 |
| Fluid AP | 57.68 |
| Sodium stearate | 6.24 |
| Minors (Perfume, Dye, Deodorant Material) | 2.40 |
| | 100.00 |

For each comparison, ten subjects had a test composition applied to one forearm and the comparison composition to the other. The compositions were rubbed on a hair covered portion for a period of approximately 3 seconds. The subjects then rated the compositions for hair pull, drag and smoothness during application and stickiness after application. The ratings were made using a nine point scale with 1 representing none of the attribute and 9 representing a lot of the attribute.

The results were as follows:

| | Average Scores | | |
| --- | --- | --- | --- |
| Attribute | I-Control | II-Control | III-Control |
| During Application | | | |
| Hair pull | 3.00–3.89 | 3.89–5.11 | 3.50–5.70 |
| Drag | 2.67–5.11 | 4.22–5.78 | 3.70–5.60 |
| Smoothness | 7.22–6.00 | 5.89–5.44 | 6.80–5.50 |
| After Application | | | |
| Stickiness | 4.00–5.44 | 5.56–6.00 | 4.10–5.90 |

It is seen that the compositions of the present invention were rated superior to the control composition in all attributes.

What is claimed is:

1. In an improved deodorant cosmetic gel stick composition comprising
   (a) from about 6% to about 70% of an aliphatic polyhydric alcohol having 2 to 3 carbon atoms and from 2 to 3 hydroxyl group;
   (b) from 3% to about 10% of a soap and
   (c) from about 0.1% to about 1% of a deodorant material wherein the improvement comprises including from about 15% to about 40% of diisopropyl adipate to reduce hair pull, drag, smoothness during application and stickiness after application.

2. A stick composition according to claim 1 wherein the amount of polyhydric alcohol is from about 15% to about 70%.

3. A stick composition according to claim 1 wherein the amount of di-isopropyl adipate is from about 15% to about 40%.

4. A stick composition according to claim 1 which in addition contains from about 10% to about 60% of a condensation product having the formula $$R(OC_2H_4)_a(OC_3H_6)_bOH$$

wherein R is selected from the group consisting of hydrogen and hydrocarbon chains having from about 2 to about 20 carbon atoms, a and b are each from about 0 to about 35 and a+b is from about 5 to about 35.

5. A stick composition according to claim 4 wherein the soap is selected from the group consisting of a sodium salt and a potassium salt of a fatty acid containing from about 14 to about 18 carbon atoms and R in the condensation product is a hydrocarbon chain having from about 4 to about 18 carbon atoms.

6. A stick composition according to claim 5 which in addition contains from about 5% to about 30% of a fatty alcohol or an ethoxylated fatty alcohol.

7. A stick composition according to claim 6 which in addition contains a monohydric alcohol selected from the group consisting of methanol, ethanol, isopropanol and n-propanol.

8. A stick composition according to claim 7 wherein the polyhydric alcohol is selected from the group consisting of ethylene glycol, propylene glycol, trimethylene glycol and glycerine.

9. A stick composition according to claim 8 wherein the soap is selected from the group consisting of sodium stearate, sodium palmitate, sodium myristate, potassium stearate and potassium palmitate.

10. A stick composition according to claim 9 wherein the polyhydric alcohol is propylene glycol.

11. A stick composition according to claim 9 in which the fatty alcohol is myristyl alcohol.

* * * * *